(12) United States Patent
Ron et al.

(10) Patent No.: US 6,204,270 B1
(45) Date of Patent: Mar. 20, 2001

(54) OPHTHALMIC AND MUCOSAL PREPARATIONS

(76) Inventors: Eyal S. Ron, 7 Coach Rd., Lexington, MA (US) 02420; Dov Tamarkin, Har Hila 537, Macabim (IL)

( * ) Notice: Subject to any disclaimer, the term of this patent is extended or adjusted under 35 U.S.C. 154(b) by 0 days.

(21) Appl. No.: 09/439,636

(22) Filed: Nov. 12, 1999

(51) Int. Cl.[7] .................. A61K 31/52; A61K 31/445
(52) U.S. Cl. ............................................ 514/263; 514/323
(58) Field of Search ..................................... 514/323, 263

(56) References Cited

U.S. PATENT DOCUMENTS

| | | | |
|---|---|---|---|
| 5,370,870 | * | 12/1994 | Wong .................................. 424/85.1 |
| 5,443,824 | * | 8/1995 | Piacquadio ........................ 424/78.02 |
| 5,502,066 | * | 3/1996 | Heinemann et al. ................ 514/360 |
| 5,593,990 | * | 1/1997 | D'Amato .......................... 514/235.2 |

* cited by examiner

*Primary Examiner*—Raymond Henley, III

(57) ABSTRACT

A composition to treat mucosal disorders includes a therapeutically effective quantity of an anti-TNF-α agent and a mucoadhessive delivery system.

20 Claims, No Drawings

OPHTHALMIC AND MUCOSAL PREPARATIONS

FIELD OF THE INVENTION

The invention relates to a composition for topical application to mucosal membranes in order to treat disorders and/or to reduce or prevent the occurrence of such disorders comprising, an anti-TNF-α agent and a vehicle.

BACKGROUND

Introduction

Cytokine response patterns play an important role in inflammatory, infectious and autoimmune diseases, in both humans and mammals. Tumor necrosis factor-alpha (TNF-α), also termed "Cachectin", is a naturally occurring cytokine with many functions in the human immune system. It is thought to medicate both protective and detrimental manifestations of the inflammatory response. Over-expression of TNF-α has been linked to inflammation and to higher rates of apoptosis, resulting in untoward clinical manifestations.

TNF-α in eye disorders

A coherent view of the role of TNF-α in inflammatory eye disease is emerging as a result of studies both in man and in experimental animals. TNF-α is found in ocular tissues obtained from patients with intra-ocular inflammation (uveitis). Studies have shown that TNF-α induces uveitis in the rabbit eye (Kulkarni P S and Srinivasin B D, Exp Eye Res 1988; 46(4):631–633). Common complications of ocular inflammation such as glaucoma, keratic precipitates, retinal (macular) oedema and neovascularization may be mediated by TNF-α.

The blood-retinal barrier (BRB), which is formed by the retinal vascular endothelium and the retinal pigment epithelium, is responsible for controlling the passage of cells and molecules into the neuroretina. During ocular inflammatory diseases, however, this selective control is altered due to changes in BRB function such as increased permeability and leukocyte recruitment. The causative factors leading to barrier breakdown are not entirely understood, although cytokines have recently been implicated. In vivo studies, using a rat model revealed that elevated levels of TNF-α cause an in crease in the BRB permeability, thus inducing the infiltration of inflammatory cells (Bamforth SD et al, Acta Neuropathol (Berl) 1996; 91(6):624–632).

Experimental autoimmune uveoretinitis (EAU) serves as a model for several immune-mediated diseases that affect the eye in humans and it has been postulated that TNF-α has an important pro-inflammatory role in EAU and possibly in human uveitis. It has been shown that neutralization of systemic TNF-α ameliorates EAU (Sartani G et al, Invest Ophthalmol Vis Sci 1996; 37(11):2211–2218). In vitro studies have also demonstrated that conjunctival epithelial cells secreted the pro-inflammatory cytokines, TNF-α in response to stimuli, suggesting that these cells may contribute to the pathogenesis of human ocular diseases by production of these pro-inflammatory cytokines (Gamache D A et al, Ocul Immunol Inflamm 1997; 5(2): 117–128).

Ultraviolet (UV) irradiation exposure represents a significant environmental and occupational hazard that can cause acute and chronic inflammatory changes in the exposed cornea, and laboratory studies have shown that acute UV exposure leads to a significant increase in the production of TNF-α (Kennedy M, et al, Invest Ophthalmol Vis Sci 1997; 38(12):2483–2491).

TNF-α has the capacity to mediate neuronal or axonal injury, leading to optic neuropathy (Madigan MC et al, Neurol Res 1996; 18(2):176–184). Corneal allograft rejection culminates in a series of interactions between different classes of antigen presenting cells, cytokines and leukocytes. TNF-α was recently reported to be elevated in acute rejection of solid organ transplants (Pleyer U et al, Ocul Immunol Inflamm 1997; 5(3): 149–155). Studies demonstrate that gamma-Interferon and TNF-α exert an enhancing effect on man corneal epithelial (HCE) cells and on the adhesion of lymphocytes to HCE cells, directly or via enhancement of ICAM-1 expression (Iwata M et al, Curr Eye Res 1997; 16(8):751–760).

TNF-α in disorders of the oral cavity

TNF-α in eye disorders

TNF-α is involved in the formation and exacerbation of oral cavity disorders, as revealed by human studies as well as in experimental animals. Recurrent Aphthous Ulcers (RAU's), commonly known as canker sores, are benign open sores in the mouth, which appear as painful white or yellow sores (ulcers) surrounded by a bright red area. The cause is unknown. Much evidence suggests that RAU is an immunologically mediated disease. Parallels have been drawn between the immunopathologic characteristics of aphthous lesions with local increases in the ratio of CD4: CD8 infiltrating T-lymphocytes and induction of class II major histocompatibility molecules on keratinocytes and epithelial cells. The latter observation suggests an active cytokine response. Recent studies indicate a possible etiologic role for locally produced TNF-α in RAU. Significantly greater amounts of TNF-α were released from unstimulated monocyte- enriched and monocytedepleted leukocyte fractions in active RAU compared with those from healthy control donors, suggesting that this cytokine may be associated with RAU (Taylor L. J.; Bagg J., Walker D. M. and Peters T. J., J. Oral Pathol. Med., 1992; 21(1):21–25). Further studies have demonstrated that TNF-α production is increased in peripheral blood lymphocytes of healthy patients with RAU (MacPhail LA. and Greenspan J. S., Oral Dis 1997; 3 Suppl 1:S190–S193).

Periodontal disease is the most frequent cause of tooth loss in humans and is the most prevalent disease associated with bone loss, including osteoporosis. Bacteria that colonize the tooth surface, leading to inflammation and bone resorption initiate periodontal destruction. In vivo studies have shown that the pathologic process of periodontitis is due to TNF-α activity (Assuma R. et al, J Immunol 1998; 160(1):403–409). Autoimmune disorders of the oral cavity, e.g., oral lichen have also been associated with elevated levels of TNF-α (Zahran F. M., Egypt Dent J 1995; 41(4): 1363–1366).

In conclusion, it is conceivable that various ophthalmic and mucosal disorders are associated with overexpression of pro-inflammatory cytokines, and that attenuation of those cytokines may be beneficial in the treatment of such disorders.

Current uses of anti-TNF-α agents

Various anti-TNF-α agents have been proposed as therapeutic modalities for inflammatory and autoimmune disorders. Pentoxifylline has been claimed to affect TNF-α related disorders (U.S. Pat. Nos. 5,370,870; 5,502,066; 5,585,380; 5,641,783; 5,643,875; 5,672,622; 5,730,975). Oral administration of pentoxifylline has been shown experimentally to exert a beneficial effect on thyroid associated ophthalmopathy (TAO) and the response was correlated with reduction of TNF-α levels (Balazs C et al, J Clin Endocrinol Metab 1997; 82(6):1999–2002). However, none of the above mentioned patents and publications relates to the topical use of pentoxifylline in eye disorders. Other xantliines, e.g., propentofylline, also possess anti-TNF-α properties, but none has been reported to be used topically on the mucosal tissues of the eye and the oral cavity.

Thalidomide is another known inhibitor of TNF-α has been demonstrated effective in TNF-related disorders, and was approved by the FDA for the treatment of RAU in patients with AIDS or cancer. Thalidomide is given orally to patient, in doses of 100 mg, four times per day, thus exposing them to known adverse effects of this drug. U.S. Pat. Nos. 5,385,901; 5,502,066; 5,635,517 and 5,712,291 claim the use of thalidomide in TNF-α—related disorders, however, none of said patents relates to a topical application of thalidomide or to topical delivery systems for this agent onto mucosal tissues.

Topical delivery of anti- TNF-α agents

Direct topical application of pharmacological agents onto mucosal tissues the eye and the mouse cavity has not been reported in the prior art. Due to the facile clearance of those agents, via washing by tears and mouth fluids, specific formulations, designed to prolong the availability of the therapeutic product on the surface and to enable sustained release of the active ingredient have been developed. Mucoadhesion is generally understood as the ability of a biological or synthetic material to "stick" to mucous membrane, resulting in adherence of the material to the tissue for protracted period of time. Mucoadhesive materials are generally high molecular weight polymers. These polymers entangled into the mucin layer forming a complex layer of polymers and mucin. The presence of different functional groups on the polymeric backbone is important as well. It is known that hydrogen bonding plays an important roll in adhesion (Morrtazavi, SA, *Intl J Pharm* 1995;124(2):173).

SUMMARY OF THE INVENTION

The present invention relates to a composition to treat mucosal disorders of the eye and oral cavity, comprising a therapeutically effective dose of an anti- TNF-α agent and a delivery system, by, topical application.

The anti- TNF-α agent may be either a chemical or a biological substance. The anti- TNF-α agent may be selected from known agents, which inhibit TNF-α production, neutralize TNF-α or suppress of TNF-α pro-inflammatory signal transduction cascade.

In a more specific embodiment, the anti- TNF-α agent is thalidomiide or thalidomide analog or a xanthines, such as pentoxifylline and propentofylline.

The composition of the invention contains a vehicle, suitable for ophthalmic or mucosal administration. Film-forming hydrogel systems, comprising mucoadhesive polymers, are particularly preferred as vehicle. The composition of the invention may also contain agents chosen from the list of local anesthetic ingredients, preservatives, anti-bacterial, anti-fungal or anti-viral agents.

The present invention further relates to a method of treating ophthalmic disorders, particularly eye infection, inflammation and allergy, comprising topical application of said composition onto the affected area.

The present invention further relates to a method of treating disorders of the oral cavity, comprising topical application of said composition onto the affected area.

DETAILED DESCRIPTION OF THE INVENTION

The present invention relates to a composition to to treat mucosal disorders of the eye and oral cavity comprising of a therapeutically effective dose of an anti- TNF-α agent and a delivery system, suitable for topical application onto mucosal tissues.

Anti- TNF-α agents are chemically or biologically-originated materials that suppress the pro-inflammatory effect of TNF-α via various mechanisms, including, but not limited to a) inhibiting the formation of TNF-α; b) suppressing TNF-α interaction with its receptors; c) neutralization by direct or indirect interaction.

Examples of chemical anti- TNF-α agents are known pharmaceutical materials, such as pentoxifylline, propentofylline, torbafylline (and other related xanthines), amiloride, chloroquine, thalidomide and structural analogs thereof Examples for biological anti-TNF-α agents are anti-TNF-α antibodies and soluble TNF-α receptors. Additional compounds are those that impair the signal transduction cascade from the receptor to other functional organs of the living cell. Such active agents, as well additional compounds, that are capable of inhibiting the production or otherwise suppressing the pro-inflammatory effects of TNF-α can be used in the treatment of ophthalmic diseases.

TNF-α—related eye disorders, to be treated according to the present invention include intraocular inflammation (uveitis), ocular inflammation, such as glaucoma, keratic precipitates, retinal (macular) oedema and neovascularization, diabetic retinopathy, bacterial, fungal and viral conjunctivitis, macular degeneration and inflammation response after intra-ocular lens implantation. Secondary inflammation, accompanying bacterial, fungal or viral infection as well as eye injury are also examples of pro-inflammatory TNF-α-related ophthalmic disorders.

TNF-α—related disorders of the oral cavity include recurrent aphthous ulcers, autoimmune disorders of the oral cavity, periodontitis, bacterial, fungal and viral infections of the oral cavity.

Advantages of the system of the invention over existing systemic anti-cytokine therapies in ophthalmic and oral disorders:

1. The composition of the invention provides targeting of the drug to the site of disease;
2. The composition of the invention requires lower frequency of administration due to controlled release system;
3. Due to the local administration, lower doses of the active agent are being administered, resulting in less side effects;
4. The anti-TNF-α agent can be selected to exert specific immunomodulatory activities, as opposed to the commonly used non-specific anti-inflammatory substances.
5. Due to the local administration of the composition of the invention, the risk of systemic TNF-α inhibition is avoided. This is particularly important when excessive TNF-α is needed for the function of the body (for example, in cancer, high TNF-α is beneficial).

EXAMPLES

1. A composition comprising of 1% Carbomer 934P (Film former, BF Goodrich, Cincinnati, Ohio), 0.5% emulsifiers (sorbitan sesquioleate) and 5% Pentoxiphylline in purified water brought to pH 6 by adding NaOH. The system exhibit viscosity, adherence to tissue (tested between 2 fingers)
2. A delivery system (hydrogel) comprising of 0.25% Carbomer 941 (film former, BF Goodrich, Cincinnati, Ohio), 0.35% CMC (film former, FMC, N.J.) are dissolved in dibasic sodium phosphate buffer (pH 5.5). 1% of Pentoxiphylline is added to the hydrogel solution.
3. A delivery system was made by adding to purified water: 2% propylene glycol, 0.5% Carbomer 934P, and brought to H 5.5–6 by the addition of NaOH.

4. A delivery system made of PEG-8, glycerin, water, carbomer 974-P, acesulfame-K, Chlorothymol (preservative), eugenol (flavor), FD&C Red #4 (color)
5. Polyethylene glycols (vehicle), propylene glycol (vehicle, solvent), purified water (solvent), sodium saccharin (sweetener), sorbic acid (preservative).
6. Zinc chloride (astringent), allantoin (skin protectant), carbomer 941 (film former), edetate disodium (chelating agent), peppermint oil (flavor), polyethylene glycol (vehicle), polysorbate 60 (surfactant), propyl gallate (antioxidant), propylene glycol (vehicle), purified water (solvent), povidone (film former), sodium saccharin (sweetener), sorbic acid (preservative), stearyl alcohol (film former).
7. Dyclonine hydrochloride (anesthetic), citric acid (pH adjustment), flavor, hydroxylated lanolin and petrolatum (vehicles), propylene glycol (vehicle), purified water (solvent), PVP (thickener), yellow wax (thickener).

We claim:

1. A composition to treat mucosal disorders comprising a therapeutically effective quantity of an anti-TNF-α agent and a mucoadhesive delivery system, wherein the anti-TNF-α agent comprises a TNF-α neutralizing agent.

2. A composition to treat mucosal disorders comprising a therapeutically effective quantity of an anti-TNF-α agent and a mucoadhesive delivery system, wherein the anti-TNF-α agent is a suppresser of the TNF-α signal transduction cascade.

3. A composition of to treat mucosal disorders comprising a therapeutically effective quantity of an anti-TNF-α agent and a mucoadhesive delivery system wherein the anti-TNF-α agent is a xanthine or a xanthine derivative.

4. A composition of claim 1, 2, or 3, where the anti-TNF-α agent is at a concentration of 0.01–10% by weight.

5. A composition of claim 3, where the xanthine or xanthine derivative is selected from the group consisting of pentoxifylline, propentofylline, and torbafylline.

6. A composition of claim 1, 2, or 3 wherein the delivery system is a film-forming hydrogel system.

7. A composition of claim 1, 2, or 3 wherein the delivery system contains mucoadhesive polymers.

8. A composition of claim 1, 2, or 3 where the vehicles adhere to the mucosal membrane and ascertain controlled release of the active agent into its site of action.

9. A composition of claim 1, 2, or 3, further comprising a local anesthetic.

10. A composition of claim 1, 2, or 3, further comprising taste ingredients.

11. A composition of claim 1. 2, or 3, further comprising preservatives.

12. A composition of claim 1, 2, or 3, further comprising anti-bacterial agents.

13. A composition of claim 1, 2, or 3 further comprising anti-viral agents.

14. A method of treating or preventing eye disorders, comprising topical application of a composition comprising a therapeutically effective quantity of an anti-TNF-α agent selected from a group consisting of TNF-α neutralizing agents suppressors of the TNF-α signal transduction cascade and xanthine or xanthine derivatives and a mucoadhesive delivery system onto the affected eye.

15. A method of treating or preventing eye disorders of claim 14, wherein the disorder is associated with elevated levels of TNF-α, and the method includes topical application of the anti-TNF-α agent composition.

16. The method of claim 15, wherein the eye disorder is selected from the list of uveitis, glaucoma, keratic precipitates, retinal (macular) oedema and neovascularization, diabetic retinopathy, bacterial, fungal and viral conjunctivitis, macular degeneration and inflammation response after intra-ocular lens implantation.

17. The method of claim 15, wherein the eye disorder comprises secondary inflammation, accompanying bacterial, fungal or viral infection as well as eye injury.

18. A method of treating or preventing oral cavity disorders, associated with elevated levels of pro-inflammatory cytokines, comprising topical application of a composition comprising a therapeutically effective quantity of an anti-TNF-α agent selected from a group consisting of TNF-α neutralizing agents, suppressors of the TNF-α signal transduction cascade, and xanthine or xanthine derivatives and a mucoadhesive delivery system onto the affected area.

19. A method of treating or preventing inflammatory and autoimmune disorders of the oral cavity, periodontitis, bacterial, fungal and viral infections, comprising topical application of a composition comprising a therapeutically effective quantity of an anti-TNF-α agent selected from a group consisting of TNF-α neutralizing agents, suppressors of the TNF-α signal transduction cascade, and xanthine or xanthine derivatives; and a mucoadhesive delivery system onto the affected area.

20. A method of treating or preventing aphthous ulcers, affecting mucous membranes of the mouth, lips, cheeks and gums of the oral cavity, comprising topical application of a composition comprising a therapeutically effective quantity of an anti-TNF-α agent selected from a group consisting of TNF-α neutralizing agents, suppressors of the TNF-α signal transduction cascade, and xanthine or xanthine derivatives; and a mucoadhesive delivery system onto the affected area.

* * * * *